United States Patent [19]
Loos

[11] Patent Number: 6,017,302
[45] Date of Patent: Jan. 25, 2000

[54] SUBLIMINAL ACOUSTIC MANIPULATION OF NERVOUS SYSTEMS

[76] Inventor: Hendricus G. Loos, 3019 Cresta Wy., Laguna Beach, Calif. 92651

[21] Appl. No.: 08/961,907

[22] Filed: Oct. 31, 1997

[51] Int. Cl.⁷ ...................................................... A61B 5/00
[52] U.S. Cl. ............................................................ 600/28
[58] Field of Search ........................ 600/26–28; 128/897, 128/898

[56] References Cited

U.S. PATENT DOCUMENTS

| | | | |
|---|---|---|---|
| 4,124,022 | 11/1978 | Gross . | |
| 4,335,710 | 6/1982 | Williamson | 600/28 |
| 4,573,449 | 3/1986 | Warnke . | |
| 5,076,281 | 12/1991 | Gavish | 600/28 X |
| 5,123,899 | 6/1992 | Gall | 600/28 |
| 5,309,411 | 5/1994 | Huang et al. | 367/140 |
| 5,733,240 | 3/1998 | De Visser | 600/9 |

*Primary Examiner*—Samuel Gilbert

[57] ABSTRACT

In human subjects, sensory resonances can be excited by subliminal atmospheric acoustic pulses that are tuned to the resonance frequency. The ½ Hz sensory resonance affects the autonomic nervous system and may cause relaxation, drowsiness, or sexual excitement, depending on the precise acoustic frequency near ½ Hz used. The effects of the 2.5 Hz resonance include slowing of certain cortical processes, sleepiness, and disorientation. For these effects to occur, the acoustic intensity must lie in a certain deeply subliminal range. Suitable apparatus consists of a portable battery-powered source of weak subaudio acoustic radiation. The method and apparatus can be used by the general public as an aid to relaxation, sleep, or sexual arousal, and clinically for the control and perhaps treatment of insomnia, tremors, epileptic seizures, and anxiety disorders. There is further application as a nonlethal weapon that can be used in law enforcement standoff situations, for causing drowsiness and disorientation in targeted subjects. It is then preferable to use venting acoustic monopoles in the form of a device that inhales and exhales air with subaudio frequency.

17 Claims, 5 Drawing Sheets

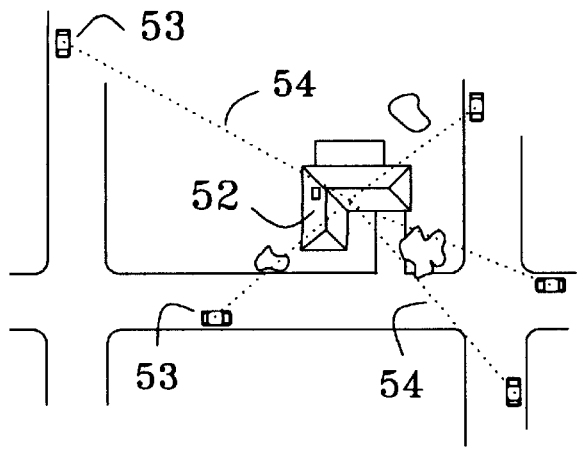
FIG. 8
SOUND PRESSURE LEVEL −61 dB
FREQUENCY 2.558 Hz
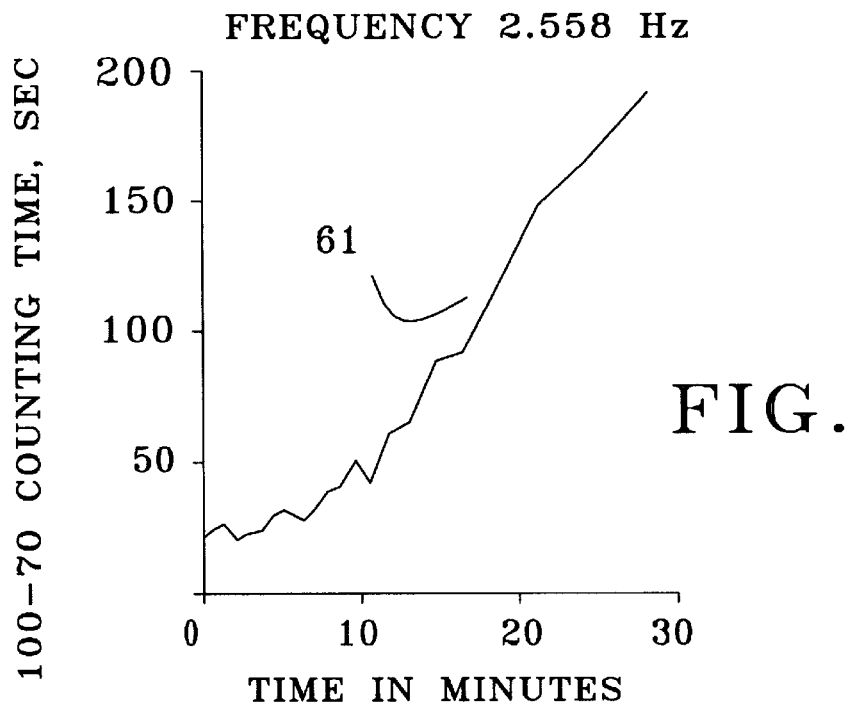
FIG. 11
FIG. 12
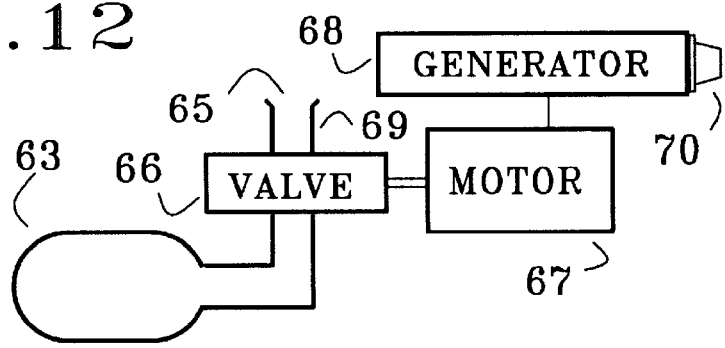

SUBLIMINAL ACOUSTIC MANIPULATION OF NERVOUS SYSTEMS

BACKGROUND OF THE INVENTION

The central nervous system can be manipulated via sensory pathways. Of interest here is a resonance method wherein periodic sensory stimulation evokes a physiological response that peaks at certain stimulus frequencies. This occurs for instance when rocking a baby, which typically provides relaxation at frequencies near ½ Hz. The peaking of the physiological response versus frequency suggests that one is dealing here with a resonance mechanism, wherein the periodic sensory signals evoke an excitation of oscillatory modes in certain neural circuits. The sensory pathway involved in the rocking example is the vestibular nerve. However, a similar relaxing response at much the same frequencies can be obtained by gently stroking a child's hair, or by administering weak heat pulses to the skin, as discussed in U.S. Pat. No. 5,800,481, Sep. 1, 1998. These three types of stimulation involve different sensory modalities, but the similarity in responses and effective frequencies suggests that the resonant neural circuitry is the same. Apparently, the resonance can be excited either via vestibular pathways or via cutaneous sensory pathways that carry tactile or temperature information.

Near 2.5 Hz another sensory resonance has been found that can be excited by weak heat pulses induced in the skin, as discussed in U.S. Pat. No. 5,800,481, Sep. 1, 1998. This sensory resonance brings on a slowing of certain cortical functions, as indicated by a pronounced increase in the time needed to silently count backward from 100 to 70 with the eyes closed. The effect is sharply dependent on frequency, as shown by a response peak a mere 0.13 Hz wide. The thermally excited 2.5 Hz resonance was found to also cause sleepiness, and after long exposure, dizziness and disorientation.

Other, more obscure types of stimulation in the form of weak magnetic fields or weak external electric fields can also cause the excitation of sensory resonances, as

SUMMARY OF THE INVENTION

Experiments have shown that atmospheric acoustic stimulation of deeply subliminal intensity can excite in a human subject the sensory resonances near ½ Hz and 2.5 Hz. The ½ Hz resonance is characterized by ptosis of the eyelids, relaxation, drowsiness, a tonic smile, tenseness, or sexual excitement, depending on the precise acoustic frequency near ½ Hz that is used. The observable effects of the 2.5 Hz resonance include a slowing of certain cortical functions, sleepiness, and, after long exposure, dizziness and disorientation. The finding that these sensory resonances can be excited by atmospheric acoustic signals of deeply subliminal intensity opens the way to an apparatus and method for acoustic manipulation of a subject's nervous system, wherein weak acoustic pulses are induced in the atmosphere at the subject's ears, and the pulse frequency is tuned to the resonance frequency of the selected sensory resonance. The method can be used by the general public for control of insomnia and anxiety, and for facilitation of relaxation and sexual arousal. Clinical use of the method includes the control and perhaps a treatment of anxiety disorders, tremors, and seizures. A suitable embodiment for these applications is a small portable battery-powered subaudio acoustic radiator which can be tuned to the resonance frequency of the selected sensory resonance.

There is an embodiment suitable for law enforcement operations in which a subject's nervous system is manipulated from a considerable distance, as in a standoff situation. Subliminal subaudio acoustic pulses at the subject's location may then be induced by acoustic waves radiating from a venting acoustic monopole, or by a pulsed air jet, especially when aimed at the subject or at another material surface, where the jet velocity fluctuations are wholly or partly converted into static pressure fluctuations.

The described physiological effects occur only if the intensity of the acoustic stimulation falls in a certain range, called the effective intensity window. This window has been measured in exploratory fashion for the 2.5 Hz resonance.

BRIEF DESCRIPTION OF THE DRAWINGS

FIG. 8 illustrates an application in a law enforcement standoff situation.

FIG. 11 shows the buildup of the physiological response to the acoustic stimulation.

FIG. 12 shows schematically an acoustic monopole operated by a rotating valve.

DETAILED DESCRIPTION OF THE INVENTION

Figure 1:
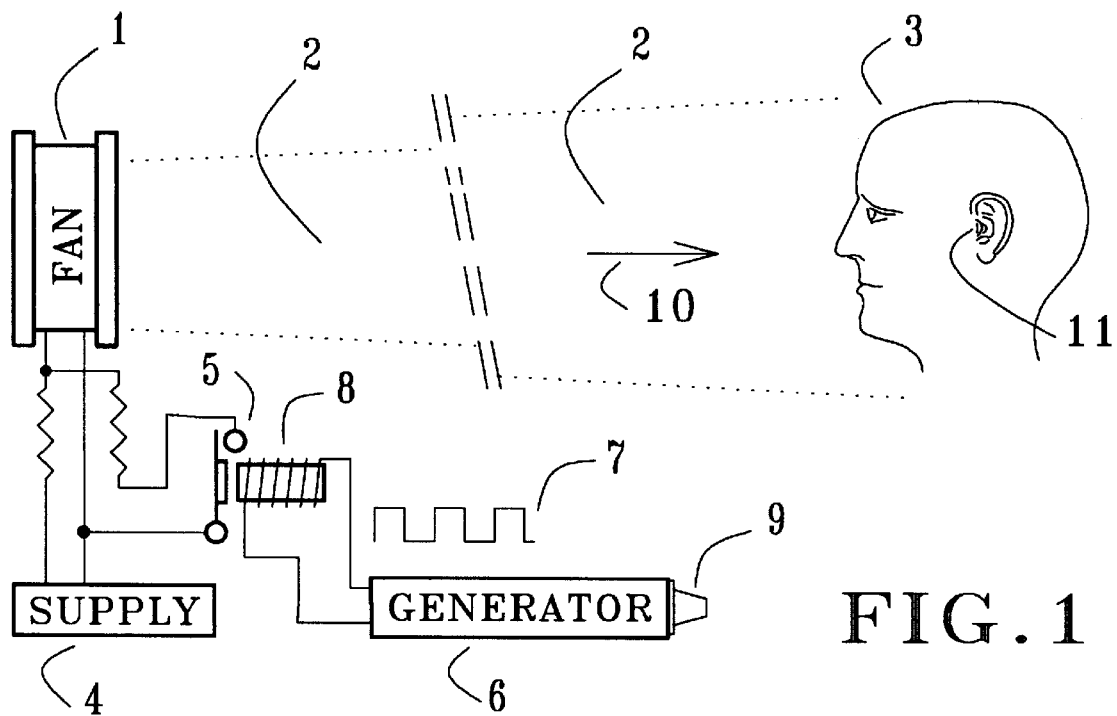
FIG. 1 illustrates a preferred embodiment wherein a modulated air jet is used for inducing subliminal acoustic pulses in the atmosphere at the subject's ears, for the purpose of manipulating the subject's nervous system.

It has been found in our laboratory that deeply subliminal atmospheric acoustic pulses with frequency near ½ Hz can evoke in a human subject a nervous system response that includes ptosis of the eyelids, relaxation, drowsiness, the feeling of pressure at a centered spot on the brow, seeing moving patterns of dark purple and greenish yellow with the eyes closed, a soft warm feeling in the stomach, a tonic smile, a "knot" in the stomach, sudden loose stool, and sexual excitement, depending on the precise acoustic frequency used. These responses show that this sensory resonance involves the autonomic nervous system.

The sharp peaking of the physiological effects with frequency is suggestive of a resonance mechanism, wherein the acoustic stimulation, although subliminal, causes excitation of a resonance in certain neural circuits. Since the frequencies and responses are similar to those for the ½ Hz sensory resonance discussed in the Background Section, it appears that the resonance excited by the described acoustic stimulation is indeed the ½ Hz sensory resonance. It has been found that the 2.5 Hz sensory resonance can be excited acoustically as well. This sensory resonance causes the slowing of certain cortical processes, sleepiness, and eventually dizziness and disorientation.

One can avoid the described physiological responses by wearing snugly fitting ear plugs. This shows that the excitation occurs via the external ear canal, so that the stimulation proceeds either through the auditory nerve or the vestibular nerve. Frequencies near ½ Hz or 2.5 Hz are far too low for stimulating the cochlear apparatus, but they are within the response range of hair cells in the vestibular end organ. Also, there exists a low-frequency acoustic path to the vestibular end organ by virtue of the ductus reuniens which provides a fluid connection between the cochlea and the vestibular organ. The narrow duct severely attenuates acoustic signals and acts as a low pass filter with a very low cutoff frequency. Subaudio acoustic signals, i.e., acoustic signals with frequencies up to 15 Hz, may perhaps penetrate to the vestibular organ with sufficient strength for stimulating the exquisitely sensitive vestibular hair cells.

For the ½ Hz and 2.5 Hz resonances, the described physiological responses are observed only if the acoustic intensity lies in a certain interval, called the effective intensity window. The acoustic intensity levels in this window are far below the human auditory threshold, so that exposed subjects do not sense the acoustic pulses in any other way than through the mentioned physiological effects. The upper limit of the effective intensity window is believed to be due to nuisance-guarding neural circuitry that blocks repetitive nuisance signals from higher processing.

The acoustic signals used for the excitation of sensory resonances have the nature of pulses. The pulses may be square, trapezoid, or triangle, or rounded versions of these shapes. However, depending on the pulse frequency, strong harmonics with frequencies in the audible range could stimulate the cochlear apparatus. This may be avoided by using sine waves or appropriately rounded other waves with low harmonic content.

The acoustic pulses occur in the atmosphere air; even when administered with earphones, the pulses at the subject's ear constitute pressure and flow pulses in the local atmospheric air.

The resonance frequencies of the ½ Hz and 2.5 Hz sensory resonances lie respectively near ½ and 2.5 Hz. The different physiological effects mentioned occur at slightly different frequencies. Thus, one can tune for drowsiness or sexual excitement, as desired. The precise resonance frequency is also expected to depend slightly on the subject and the state of the nervous and endocrine systems, but it can be measured readily by tuning the acoustic pulse frequency for maximum physiological effect. Besides the resonances near ½ and 2.5 Hz, other sensory resonances may perhaps be found, and those with resonance frequencies below 15 Hz are expected to be excitable acoustically via the vestibular nerve, since the vestibular hair cells are sensitive in this frequency range.

The finding that deeply subliminal subaudio acoustic stimulation can influence the central nervous system suggests a method and apparatus for manipulating the nervous system of a subject by inducing subliminal atmospheric acoustic pulses of subaudio frequency at the subject's ears. In doing so, one may in addition exploit the sensory resonance mechanism, but there are important applications where this is not done. For example, the subliminal acoustic manipulation of the nervous system may be used clinically for the control of tremors and seizures, by detuning the pathological oscillatory activity of neural circuits that occurs in these disorders. This may be done by choosing an acoustic frequency that is slightly different from the frequency of the pathological oscillation. The evoked neural signals then cause phase shifts which may diminish or quench the oscillation. Exploitation of the resonance mechanism by tuning the acoustic signals to the resonance frequency of a selected sensory resonance affords other forms of manipulation, such as control of insomnia and anxiety, or facilitation of sexual arousal.

For both types of manipulation, the required subliminal subaudio acoustic pulses may be induced at one or both of the subject's ears by earphones with a proper low-frequency response, acoustic waves generated by an acoustic source and propagated through the atmosphere, or by a pulsed jet of gas (which may be air), preferably directed at a material surface open to the atmosphere, such as a wall or the subject's skin or clothing. In the area of impact, especially where the surface is oriented substantially perpendicular to the jet, atmospheric pressure pulses are then generated by virtue of the ram effect, wherein flow velocity fluctuations are wholly or partly converted into static pressure fluctuations. If the material surface on which the jet impinges includes the subject's ears, then these pressure pulses cause direct stimulation of the subject, but the pulses also propagate through the atmosphere to the subject's ears by virtue of acoustic wave propagation along accessible paths.

The induction of atmospheric acoustic pulses by a pulsed air jet proceeding in the atmosphere and directed at a subject is shown in FIG. 1, where a blower 1, labeled "FAN", produces an air jet 2 that is directed at a subject 3. The fan is powered by a power supply 4, labelled "SUPPLY". At the fan, the supply voltage is modulated in pulsed fashion by a relay 5 controlled by the generator 6, labelled "GENERATOR", through voltage pulses 7 supplied to electromagnet windings 8. A user can adjust the frequency of the pulses with the tuning control 9. The pulsing of the voltage supplied to the fan causes the momentum flux 10 of the air jet to be modulated in a pulsed manner. Upon impinging on a material surface such as the skin of the subject 3, the pulsed jet induces acoustic pressure pulses at the ears 11 of the subject. The atmospheric acoustic effect of the jet is complicated by the fact that the region of the fan inlet undergoes a fluctuation of static pressure as the result of the modulation of jet momentum flux. There thus are two distinct acoustic monopoles, one at the fan inlet and the other in the area of impact of the jet on the material surface. The monopoles radiate with a phase difference that is determined by the jet velocity, the modulation frequency, and the distance between fan and impact area. The resulting sound pressure at the subject's ears can be analyzed with retarded potentials as discussed for instance by Morse and Feshbach (1953). Even a jet which does not impinge on a material surface radiates by virtue of the acoustic monopole at the fan inlet.

When skin of the subject is exposed to gas flow of the jet, or to the flow of atmospheric air entrained by the jet, the flow will fluctuate in pulsed fashion, so that a periodic heat flux occurs by convective transport and evaporation of sweat. The resulting periodic fluctuation of the skin temperature can excite a sensory resonance, as discussed in U.S. Pat. No. 5,800,481, Sep. 1, 1998. Hence, the apparatus of FIG. 1 can cause excitation of a sensory resonance via two separate sensory pathways, viz., the vestibular nerve and the afferents from cutaneous temperature receptors. The strength of the thermal stimulation depends on the skin area and type of skin exposed to the fluctuating flow. The face is particularly sensitive, especially the lips. The two-channel excitation of sensory resonances needs further investigation. In any particular situation, the vestibular channel can be blocked by using earplugs.

Figure 2:
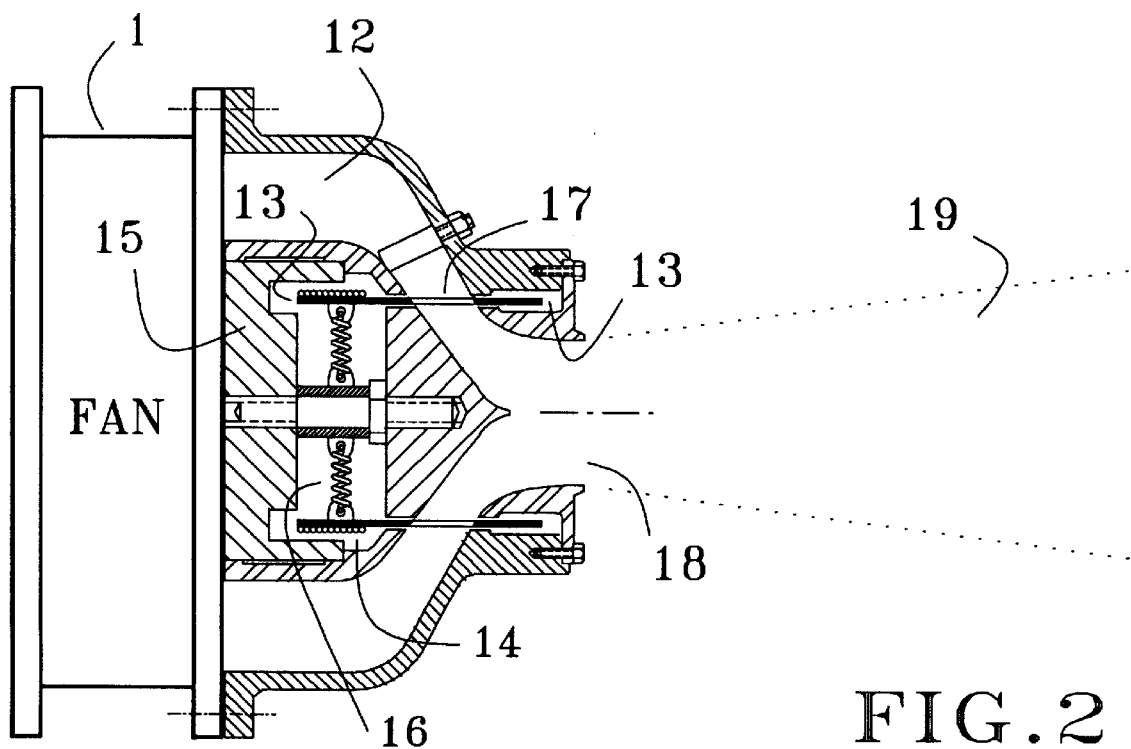
FIG. 2 shows an embodiment in which a pulsed air jet is produced by modulating the flow from a fan by a cylindrical sheet valve that is driven by a voice coil.

An air jet with pulsed momentum flux can also be obtained as illustrated in FIG. 2. Shown is a fan 1, labelled "FAN", which discharges into manifold 12. The air flow in the manifold can be partially obstructed by a sheet valve 13 in the form of a perforated cylindrical sheet. The sheet valve carries a voice coil 14 which is situated in the field of a permanent magnet 15, in the manner of conventional electromagnetic loudspeakers. When no current flows through the voice coil, the sheet valve is held in equilibrium position by springs 16. In this position, the perforation 17 in the sheet is lined up with the flow passage allowing essentially unimpeded flow through the manifold and out the exit 18, such as to form a jet 19 in the atmosphere. Sending a current pulse through the voice coil 14 causes the sheet valve to be displayed in the axial direction, thereby partially obstructing the air flow through the manifold. Owing to the low inertia of the sheet valve, the arrangement allows efficient pulse modulation of the jet momentum flux.

A somewhat different modulation system can be obtained with a rotating cylindrical sheet valve that has one or more holes along its periphery, and which is adjacent to a stationary cylindrical shroud that has corresponding holes, so that rotation of the valve causes modulation of the air flow through the holes. The valve is rotated by a stepper motor driven by voltage pulses. The latter are obtained from a generator that is controlled by a tuner.

One can also use direct acoustic wave propagation for inducing the required atmospheric acoustic pulses. It is then advantageous to employ as the source of the waves an acoustic monopole, since for these the acoustic pressure does not fall off as fast with increasing distance as for dipoles. Moreover, at the very low frequencies involved, acoustic pressure shorting across a conventional loudspeaker baffle is very severe. A sealed loudspeaker mounted in an airtight box eliminates this pressure shorting, and radiates acoustic waves with a relatively large monopole component.

An acoustic monopole may also be produced by having a source of pressurized gas vent through an orifice into the atmosphere in a pulsed fashion. The gas may be air. Alternatively, one may have a source of low-pressure air inhale atmospheric air through an orifice in pulsed fashion. These actions are easily achieved by an oscillating or rotating valve. For purposes of discussion it is convenient to introduce the concept of gaseous flux through the orifice, defined as the integral of the normal flow velocity component over an imagined surface that tightly caps the orifice, the normal component being perpendicular to the local surface element, and reckoned positive if the flow is directed into the ambient atmosphere. The gaseous flux has the dimension of $m^3/s$. For the case with a source of pressurized gas, the gaseous flux is positive and due to gas venting to the atmosphere. For the case with a source of vacuum, the gaseous flux is negative and due to atmospheric air entering the orifice. The strength of the acoustic monopole is expressed as the amplitude of the gaseous flux fluctuation, amplitude being defined as half the peak-to-peak variation. The concept of gaseous flux allows a unified discussion of venting acoustic monopoles that use a source of pressurized gas or a source of vacuum, or both.

The source of pressurized air could be a cylinder with pressurized gas, such as a $CO_2$ cartridge. For personal use, such a cartridge may last a long time because only very small acoustic monopole strengths are needed for the induction of the required weak acoustic signals. For long term and long range operation, the exhaust port of an air pump may serve as a source of pressurized air, and the intake port could be used as a source of vacuum.

A simple venting acoustic monopole is shown in FIG. 12, where the source 63 of pressurized gas, which may be air, is connected to a conduit 69 which has an orifice 65 that is open to the atmosphere. A rotating valve 66 labelled "VALVE" controls the gaseous flux through the orifice. The valve is rotated by a stepper motor 67 labelled "MOTOR", driven by voltage pulses from the generator 68 labelled "GENERATOR". The motor speed is determined by the frequency of the voltage pulses. This frequency can be selected by the tuner 70, which therefore controls the frequency of the acoustic pulses emited by the orifice 65. For the simple orifice shown, boundary layer separation may occur in the outflow, so that the air pulses emerge in the form of jets. This causes dipole and higher multipole components in the radiated acoustic field. If desired, such radiation components can be avoided or diminished by placing a spherically or dome shaped fine mesh screen over the orifice 65. Instead of holding pressurized gas, the source 63 may hold a vacuum. In either case, the pulsing of the gaseous flux causes radiation of monopole-type acoustic waves. The source 63 may be replenished by a pump.

Figure 3:
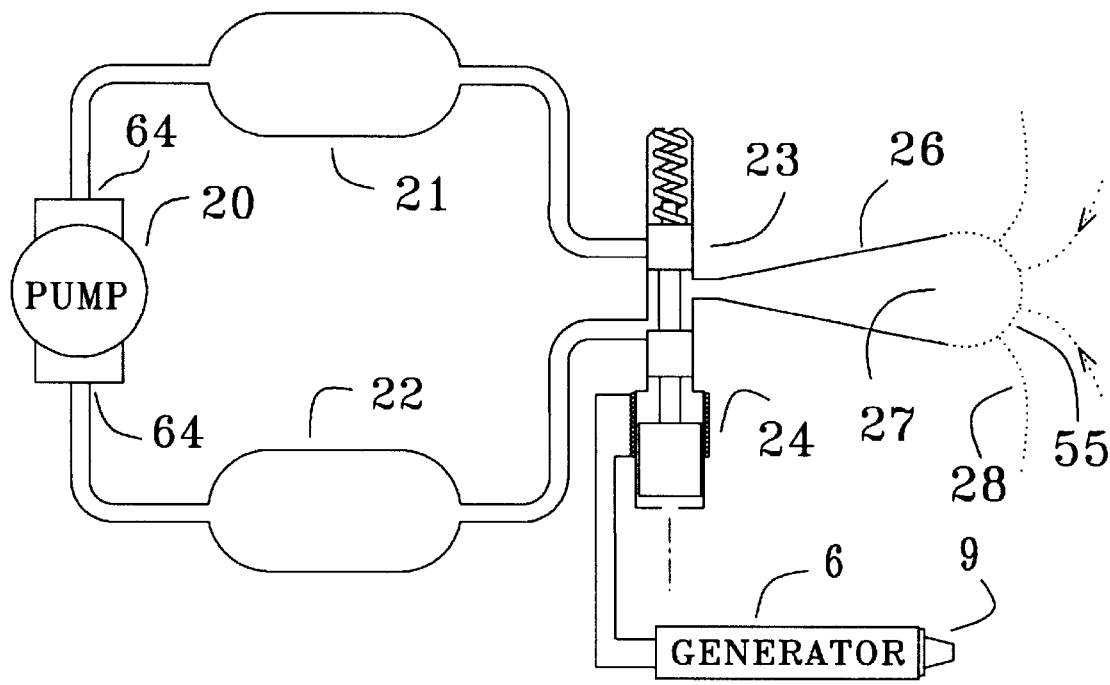
FIG. 3 shows schematically an acoustic monopole operated by a solenoid valve.

Push-pull operation can be achieved in the manner shown in FIG. 3. An air pump 20, labelled "PUMP", with flow ports 64, pressurizes the pressure vessel 21 while drawing a vacuum in the vacuum vessel 22. A valve 23 is operated by the solenoid 24 such as to alternately admit high and low pressure air to the conduit 26. The latter vents to the atmosphere through a screen 55 placed across an orifice 27 that is open to the atmosphere. The valve is controlled by an oscillator consisting of the solenoid 24, which is connected to the pulse generator 6, labelled "GENERATOR". The frequency of the electric current pulses through the solenoid is determined by the setting of the tuning control 9. This frequency is to be tuned to the resonance frequency of the sensory resonance that is to be excited. The tuning may be done manually by a user. The conduit 26 is structured as a diffuser in order to avoid boundary layer separation during the exhaust phase; the screen across the orifice 27 inhibits formation of a jet, thereby providing more nearly for a monopole type acoustic wave. During the intake phase the orifice acts as a sink; streamlines 28 of the resulting flow are illustrated. The vessels 21 and 22 smooth the flow fluctuations through the orifice that are due to the flow fluctuations through the pump; they are drawn at a relatively small scale for compactness sake. Instead of the oscillating valve 23, a rotating valve may be used, driven by a stepper motor powered by voltage pulses from a generator.

Figure 4:
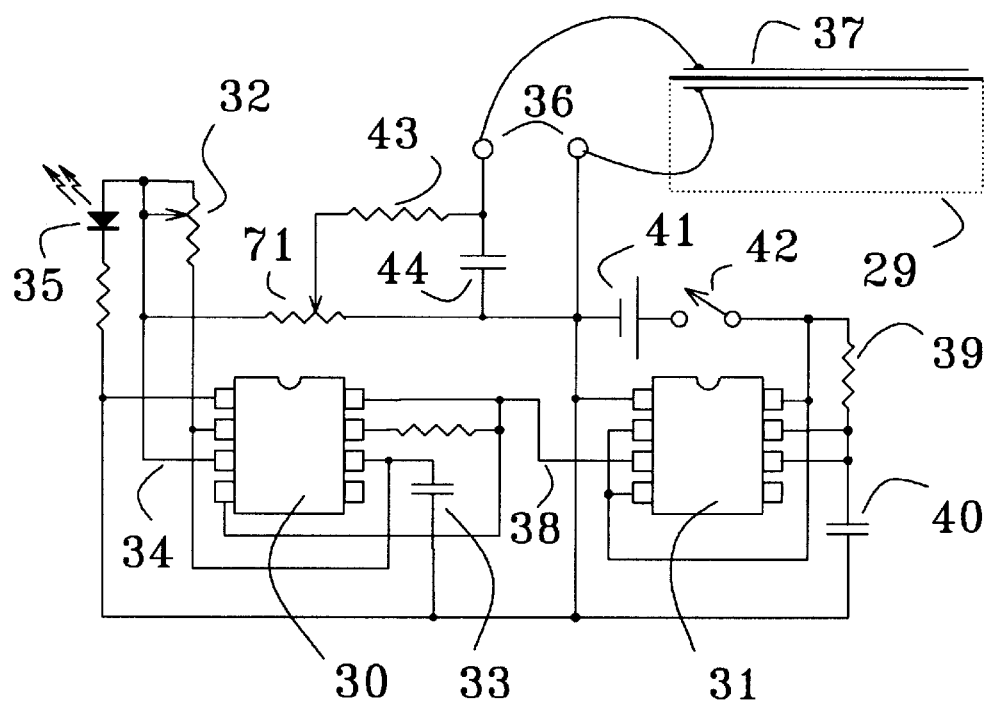
FIG. 4 shows the circuit of a simple generator for producing voltage pulses that drive a piezoelectric speaker.

Conventional loudspeakers may be used as well as the source of acoustic radiation. An example is shown in FIG. 4, where the piezoelectric transducer 37 is driven by a simple battery-powered pulse generator built around two RC timers 30 and 31. Timer 30 (Intersil ICM7555, for instance) is hooked up for astable operation; it produces a square wave voltage with a frequency determined by capacitor 33 and the potentiometer 32, which serves as a tuner that may be operated by a user. The square wave voltage at output 34 drives the LED 35, and appears at one of the output terminals 36, after voltage division by potentiometer 71. The other output is connected to the negative supply. The output terminals 36 are connected to the piezoelectric speaker. Automatic shutoff of the voltage that powers the timer 30 at point 38 is provided by a second timer 31, hooked up for monostable operation. Shutoff occurs after a time interval determined by resistor 39 and capacitor 40. Timer 31 is powered by a 9 Volt battery 41, via a switch 42. Optional rounding of the square wave is done by an RC circuit consisting of a resistor 43 and capacitor 44. An optional airtight enclosure 29 may be used for the speaker 37, in order to enhance the monopole component of the radiated acoustic signal. Instead of a piezoelectric speaker one may use an electromagnetic loudspeaker with a voice coil. Because of the low impedance of the voice coil, a resistor must then be included in the output circuitry in order to keep the output currents to low values such as to allow battery powering of the device. Small voice coil currents are sufficient for the low acoustic powers required.

Low pulse frequencies can be monitored with the LED 35 of FIG. 3. The LED blinks on and off with the square wave, and it doubles as a power indicator. The pulse frequency can be determined by reading a clock and counting the LED light pulses. For higher frequencies a monitoring LED can still be used, if it is driven by a signal obtained by frequency division of the generator signal.

The automatic shutoff described above is an example for automatic control of the generated voltage; more sophisticated forms of control involve automatic frequency sequences. A computer that runs a simple timing program can be used for the generation of all sorts of square waves that can be made available at a computer port. An economic and compact version of such arrangement is provided by the Basic Stamp manufactured by Parallax Inc, Rocklin, Calif., which has an onboard EEPROM that can be programmed for the automatic control of the generated pulses, such as to provide desired on/off times, frequency schedules, or chaotic waves. The square waves can be rounded by RC circuits, and further smoothed by integration and filtering.

Figure 5:
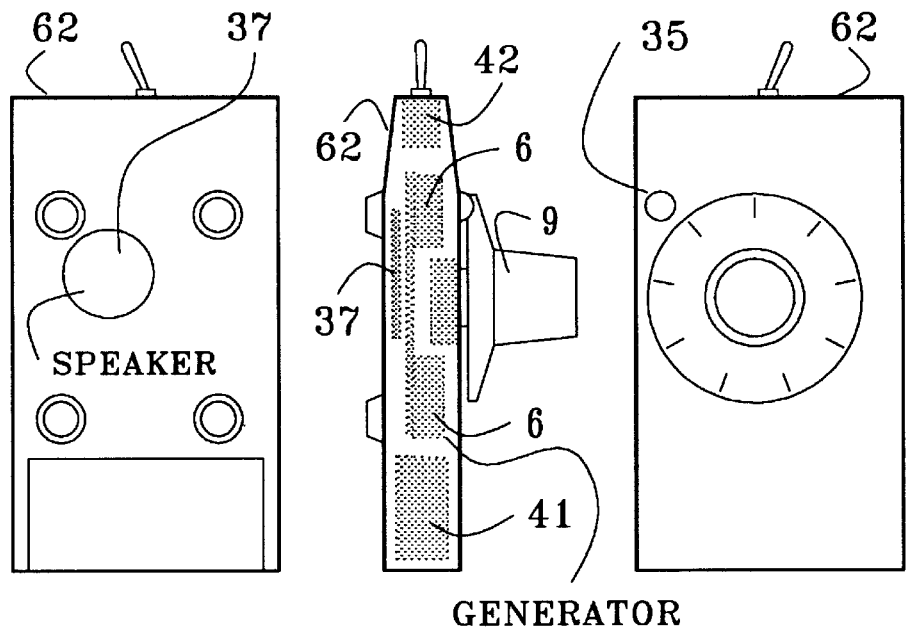
FIG. 5 depicts a portable battery-powered device that contains the circuit and the piezoelectric speaker of FIG. 4.

A compact packaging of the device such as shown of FIG. 4 is depicted in FIG. 5 where all circuit parts and the speaker, piezoelectric or voice-coil type, are contained in a small casing 62. Shown are the speaker 37, labelled "SPEAKER", driven by the generator 6, labeled "GENERATOR", with tuning control 9, LED 35, battery 41, and power switch 42. The LED doubles as a mark for the tuning control dial. With the circuit of FIG. 4, the device draws so little current that it can be used for several months as a sleeping aid, with a single 9 Volt battery.

Figure 6:
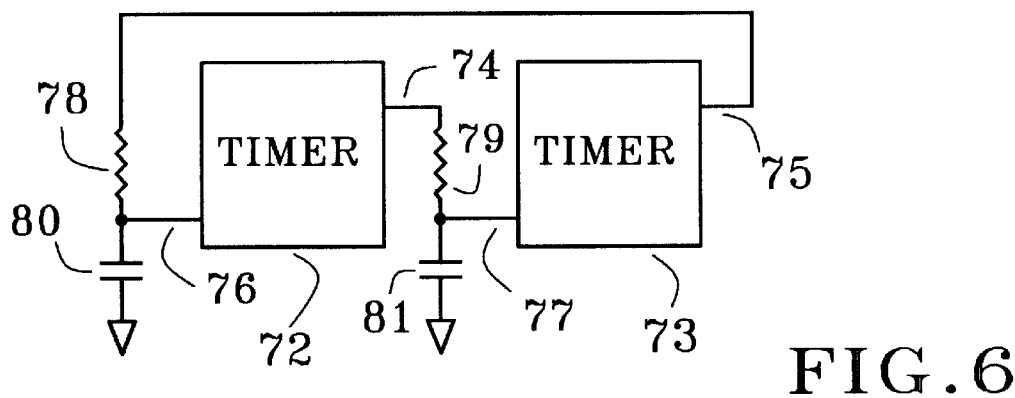
FIG. 6 shows schematically a generator for chaotic pulses.

For the purpose of thwarting habituation to the stimulation, irregular features may be introduced in the pulse train, such as small short-term variations of frequency of a chaotic or stochastic nature. Such chaotic or stochastic acoustic pulses can cause excitation of a sensory resonance, provided that the average pulse frequency is close to the appropriate sensory resonance frequency. A chaotic square wave can be generated simply by cross coupling of two timers. FIG. 6 shows such a hookup, where timers 72 and 73, each labeled "TIMER", have their output pins 74 and 75 connected crosswise to each other's control voltage pins 76 and 77, via resistors 78 and 79. The control voltage pins 76 and 75 have capacitors 80 and 81 to ground. If the timers are hooked up for astable operation with slightly different frequencies, and appropriate values are chosen for the coupling resistors and capacitors, the output of either timer is a chaotic square wave with an oval attractor. Example circuit parameters are: $R_{78}$=440K$\Omega$, $R_{79}$=700K$\Omega$, $C_{80}$=4.7 $\mu$F, $C_{81}$=4.7 $\mu$F, with $(RC)_{72}$=0.83 s and $(RC)_{73}$=1.1 s. For these parameters, the output 74 of timer 72 is a chaotic square wave with a power spectrum that has large peaks at 0.46 Hz and 0.59 Hz. The resulting chaotic wave is suitable for the excitation of the ½ Hz resonance.

Figure 7:
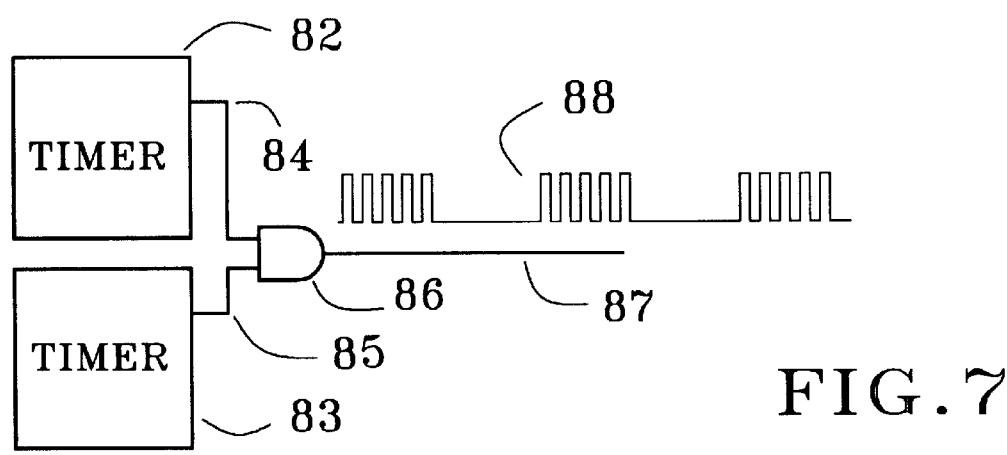
FIG. 7 depicts a circuit for generating a complex wave.

A complex wave may be used for the joint excitation of two different sensory resonances. A simple generator of a complex wave, suitable for the joint excitation of the ½ Hz autonomic resonance and the 2.5 Hz cortical resonance, is shown in FIG. 7. Timers 82 and 83 are arranged to produce square waves of frequencies $f_1$ and $f_2$ respectively, where $f_1$ is near 2.5 Hz, and $f_2$ is near ½ Hz. The outputs 84 and 85 of the timers are connected to the inputs of an AND gate 86. The output 87 of the AND gate features a square wave of frequency $f_1$, amplitude modulated by a square wave of frequency $f_2$, as indicated by the pulse train 88.

The very low frequency waves needed for the acoustic stimulation of the vestibular nerve may also be provided by a sound system in which weak subaudio pulses are added to audible audio program material. This may be done in the customary manner way of adding the currents from these signals at the inverting input of an operational amplifier. The amplitude of the pulses is chosen such that the strength of the resulting acoustic pulses lies in the effective intensity window. Experiments in our laboratory have shown that the presence of audible signals, such as music or speech, does not interfere with the excitation of sensory resonances.

The invention can also be implemented as a sound tape or CD ROM which contains audible audio program material together with subliminal subaudio signals. The recording can be done by mixing the audio and subaudio signals in the usual manner. In choosing the subaudio signal level, one must compensate for the poor frequency response of the recorder and the electronics, at the ultra low subaudio frequencies used.

The pathological oscillatory neural activity involved in epileptic seizures and Parkinson's disease is influenced by the chemical milieu of the neural circuitry involved. Since the excitation of a sensory resonance may cause a shift in chemical milieu, the pathological oscillatory activity may be influenced by the resonance. Therefore, the acoustic excitation discussed may be useful for control and perhaps treatment of tremors and seizures. Frequent use of such control may afford a treatment of the disorders by virtue of facilitation and classical conditioning.

In this as well as in the detuning method discussed before, an epileptic patient can switch on the acoustic stimulation upon sensing a seizure precursor.

Since the autonomic nervous system is influenced by the ½ sensory resonance, the acoustic excitation of the resonance may be used for the control and perhaps the treatment of anxiety disorders.

The invention can be embodied as a nonlethal weapon that remotely induces disorientation and other discomfort in targeted subjects. Large acoustic power can be obtained easily with acoustic monopoles of the type depicted in FIG. 3 or FIG. 12. If considerable distance needs to be maintained to the subject, as in a law enforcement standoff situation illustrated in FIG. 8, several monopoles can be used, and it then may become important to have phase differences between the acoustic signals of the individual monopoles arranged in such a manner as to maximize the amplitude of the resultant acoustic signal at the location 52 of the subject. Shown are four squad cars 53, each equiped with an acoustic monopole capable of generating atmospheric pulses of a frequency appropriate for the excitation of sensory resonances. The relative phases of the emitted pulses are arranged such as to compensate for differences of acoustic path lengths 54, such that the pulses arrive at the subject location 52 with substantially the same phase, resulting in constructive interference of the local acoustic waves. Such arrangement can be achieved easily by using radio signals between the monopole units, with the target distances either dialed in manually or measured automatically with a range finder. The subaudio acoustic signals can easily penetrate into a house through an open window, a chimney, or a crack under a closed door.

Some of our experiments on acoustic excitation of sensory resonances which provide a basis for the present invention will be discussed presently. Of all the responses to the excitation of the ½ Hz resonance, ptosis of the eyelids stands out for distinctness, ease of detection, and sensitivity. When voluntary control of the eyelids is relinquished, the eyelid position is determined by the relative activities of the sympathetic and parasympathetic nervous systems. There are two ways in which ptosis can be used as an indicator that the autonomic system is being affected. In the first, the subject simply relaxes the control over the eyelids, and makes no effort to correct for any drooping. The more sensitive second method requires the subject to first close the eyes about half way. While holding this eyelid position, the eye are rolled upward, while giving up voluntary control of the eyelids. With the eyeballs turned up, ptosis will decrease the amount of light admitted to the eyes, and with full ptosis the light is completely cut off. The second method is very sensitive because the pressure excerted on the eyeballs by partially closed eyelids increases parasympathetic activity. As a result, the eyelid position becomes somewhat labile, exhibiting a slight flutter. The labile state is sensitive to small shifts in the activities of the sympathetic and parasympathetic systems. The method works best when the subject is lying flat on the back and is facing a moderately lit blank wall of light color.

The frequency at which ptosis is at a maximum is called the ptosis frequency. This frequency depends somewhat on the state of the nervous and endocrine systems, and it initially undergoes a downward drift, rapid at first and slowing over time. The ptosis frequency can be followed in its downward drift by manual frequency tracking aimed at keeping ptosis at a maximum. At a fixed frequency, the early ptosis can be maintained in approximately steady state by turning the acoustic stimulation off as soon as the ptosis starts to decrease, after which the ptosis goes through an increase followed by a decline. The acoustic stimulation is turned back on as soon as the decline is perceived, and the cycle is repeated.

At fixed frequencies near ½ Hz, the ptosis cycles slowly up and down with a period ranging upward from about 3 minutes, depending on the precise acoustic frequency used. The temporal behavior of the ptosis frequency is found to depend on the acoustic pulse intensity; the drift and cycle amplitude are smaller near the low end of the effective intensity window. This suggests that the drift and the cycling of the ptosis frequency is due to chemical modulation, wherein the chemical milieu of the neural circuits involved affects the resonance frequency of these circuits, while the milieu itself is influenced by the resonance in delayed fashion. Pertinent concentrations are affected by production, diffusion, and reuptake of the substances involved. Because of the rather long characteristic time of the ptosis frequency shift, as shown for instance by the cycle period lasting 3 minutes or longer, it is suspected that diffusion plays a rate-controlling role in the process.

The resonance frequencies for the different components of the ½ Hz sensory resonance have been measured, using acoustic sine waves with a sound pressure of $2 \times 10^{-9}$ N/m² at the subject's left ear. Ptosis reached a steady state at a frequency of 0.545 Hz. Sexual excitement occurred at two frequencies, 0.530 Hz and 0.597 Hz, respectively below and above the steady-state ptosis frequency. For frequencies of 0.480 Hz and 0.527 Hz the subject fell asleep, whereas tenseness was experienced in the range from 0.600 to 0.617 Hz.

The resonance near 2.5 Hz may be detected as a pronounced increase in the time needed to silently count backward from 100 to 70, with the eyes closed. The counting is done with the "silent voice" which involves motor activation of the larynx appropriate to the numbers to be uttered, but without passage of air or movement of mouth muscles. The motor activation causes a feedback in the form of a visceral stress sensation in the larynx. Counting with the silent voice is different from merely thinking of the numbers, which does not produce a stress sensation, and is not a sensitive detector of the resonant state. The larynx stress feedback constitutes a visceral input into the brain and may thus influence the amplitude of the resonance. This unwanted influence is kept to a minimum by using the count sparingly in experiment runs. Since counting is a cortical process, the 2.5 Hz resonance is called a cortical sensory resonance, in distinction with the autonomic resonance that occurs near ½ Hz. In addition to affecting the silent counting, the 2.5 Hz resonance is expected to influence other cortical processes as well. It has also been found to have a sleep inducing effect. Very long exposures cause dizziness and disorientation. The frequency of 2.5 Hz raises concerns about kindling of epileptic seizures; therefore, the general public should not use the 2.5 Hz resonance unless this concern has been laid to rest through further experiments.

The sensitivity and numerical nature of the silent count makes it a very suitable detector of the 2.5 Hz sensory resonance. It therefore has been used for experiments of frequency response and effective intensity window. In these experiments, rounded square wave acoustic pulses were produced with a frequency that was slowly diminished by computer, and the subject's 100–70 counting time was recorded for certain frequencies. The acoustic transducer was a small loudspeaker mounted in a sealed cabinet such as to provide acoustic monopole radiation. At fixed frequency, the acoustic monopole strenght in m³/s varies linearly with the voice coil current, with a constant of proportionality that can be calculated from measured speaker dome excursions for given currents. The sound pressure level at the entrance of the subject's nearest external ear canal can be expressed in terms of the acoustic monopole strength and the distance from the loudspeaker. For each experiment run, the sound pressure level at the entrance of the subject's external ear canal can thus be calculated from the measured amplitude of the voice coil current and the pulse frequency. Since for the subaudio frequencies the distance from the acoustic radiator to the subject's ear is much smaller than the wavelength of the sound, the near-field approximation was used in this calculation. The sound pressure level was expressed in dB relative to the reference sound pressure of $2 \times 10^{-5}$ N/m². This reference pressure is traditionally used in the context of human hearing, and it represents about the normal minimum human hearing threshold at 1.8 KHz.

Figure 9:
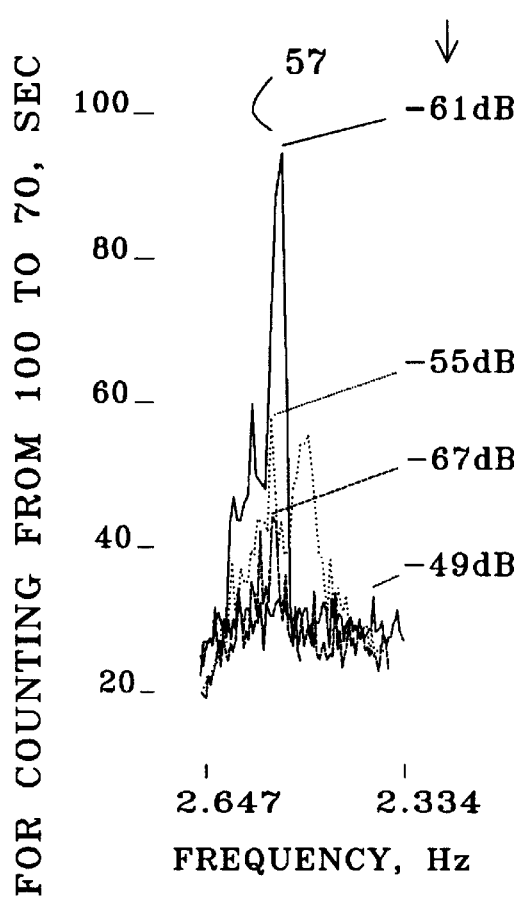
FIG. 9 contains experimental data that show excitation of the sensory resonance near 2.5 Hz, and the effective intensity window.
Figure 9:
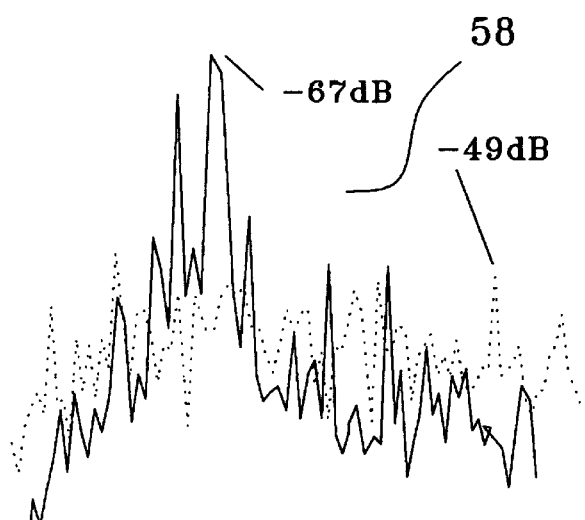

FIG. 9 shows the result of experiment runs at sound pressure levels of −67, −61, −55, and −49 dB. Plotted are the subject's 100–70 counting time versus pulse frequency in a narrow range near 2.5 Hz. Resonance is evident from the sharp peak 57 in the graph for the sound pressure level of −61 dB. The graphs also reveal the effective intensity window for the stimulation, as can be seen by comparing the magnitude of the peaks for the different sound pressure levels. For increasing intensity, the magnitude of the peak first increases but then decreases, and no significant peak shows up in the graph for the largest sound pressure of −49 dB; this can be seen better from the insert 58, which shows the graphs for −67 and −49 dB in a magnified scale. It follows that the effective intensity window extends approximately from −73 to −49 dB, in terms of the sound pressure level at the entrance of the subject's external ear canal.

Figure 10:
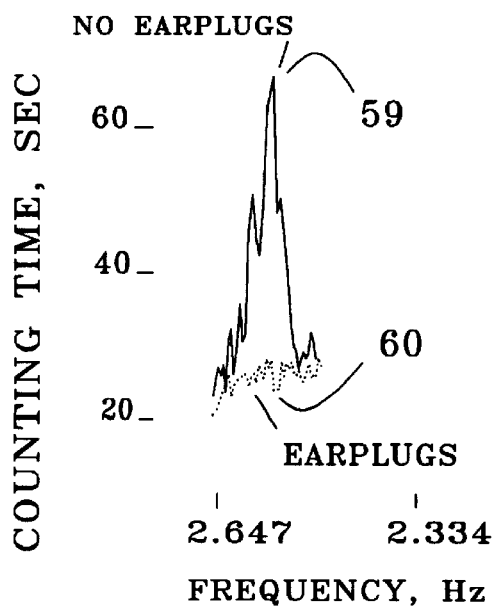
FIG. 10 depicts experimental data showing that the sensory excitation occurs via the ear canal.

The physiological response to the 2.5 Hz acoustic stimulation can be avoided by wearing earplugs. FIG. 10 is a plot of the 100–70 counting time versus acoustic pulse frequency, with and without earplugs. The sound pressure level at the entrance of the subject's external ear canal was −6 dB for both runs. Without earplugs the counting time has the peak 59, but no significant peak is seen in graph 60 for the run in which the subject used earplugs. Two conclusions can be reached from these results. First, in the experiments the 2.5 Hz resonance is essentially excited acoustically rather than through the magnetic field induced by the voice coil currents in the loudspeaker. Second, it follows that the exciting sound essentially propagates via the external ear canal, instead of through the skin and bones in the area of the ears, or via cutaneous mechanoreceptors in the skin at large.

To answer the question whether the acoustic excitation of the 2.5 Hz sensory resonance occurs perhaps through the cochlear nerve, one needs to consider the human auditory threshold curve such as shown, for instance, by Thomson (1967). The curve has a minimum near 1.8 KHz where the threshold sound pressure level is 0 dB, by definition. At 10 Hz the threshold is 105 dB. Hence, the pronounced acoustic excitation of the sensory resonance shown in FIG. 9 for a sound pressure level of −61 dB is 166 dB below the auditory threshold at 10 Hz. The excitation occurs near 2.5 Hz, and at that frequency, the auditory threshold is even higher than at 10 Hz. Although the curve in Thomson's book does not go below 10 Hz, linear extrapolation suggests the estimate of 135 dB for the threshold at 2.5 Hz, bringing the sound pressure level that is effective for acoustic excitation of the sensory resonance to 196 dB below the estimated threshold at the frequency near 2.5 Hz used. This result all but rules out excitation via the cochlear nerve.

Chemical modulation may be the cause for the small frequency difference for peaks 57 and 59 in FIGS. 9 and 10, for the sound pressure level of −61 dB; these peaks occur respectively at 2.516 and 2.553 Hz.

The physiological response to the excitation of the sensory resonances at a fixed stimulus frequency is not immediate but builds over time. An example is shown in FIG. 11, where the graph 61 depicts the measured 100–70 time plotted versus elapsed time, upon application of acoustic pulses of 2.558 Hz frequency and a sound pressure level of −61 dB. The graph shows that the response is initially delayed over about 5 minutes; thereafter it increases, and at about 22 minutes the slope is seen to decrease somewhat. Other experiments have shown a counting time that eventually settles on a plateau, or even starts on a decline. Chemical modulation and habituation could account for these features. The response curve depends strongly on initial conditions.

The method is expected to be effective also on certain animals, and applications to animal control are therefore envisioned. The nervous system of mammals is similar to that of humans, so that the sensory resonances are expected to exist, albeit with different frequencies. Accordingly, in the present invention subjects are mammals.

The described method and apparatus can be used beneficially by the general public and in clinical work. Unfortunately however, there is the possibility of mischievous use as well. For instance, with small modifications the method of FIG. 1 can be employed to imperceptibly modulate the air flow in air conditioning or heating systems that serve a home, office building, or embassy, for covert manipulation of the nervous systems of occupants.

The invention is not limited by the embodiments shown in the drawings and described in the specification, which are given by way of example and not of limitation, but only in accordance with the scope of the appended claims.

REFERENCES

P. M. Morse and H. Feshbach, METHODS OF THEORETICAL PHYSICS, McGraw-Hill, New York, 1953

R. F. Thomson, FOUNDATIONS OF PHYSIOLOGICAL PSYCHOLOGY, Harper & Row, New York 1967

I claim:

1. Apparatus for manipulating the nervous system of a subject, the subject having an ear, comprising:

generator means for generating voltage pulses;

induction means, connected to the generator means and responsive to the voltage pulses, for inducing at the ear subliminal atmospheric acoustic pulses with a pulse frequency less than 15 Hz.

2. The apparatus according to claim 1, further comprising means for automatically controlling the voltage pulses.

3. The apparatus according to claim 1, further comprising means for monitoring the voltage pulses.

4. The apparatus according to claim 1, for exciting in the subject a sensory resonance that occurs at a resonance frequency less than 15 Hz, the apparatus further comprising tuning means for enabling a user to tune the pulse frequency to the resonance frequency.

5. The apparatus according to claim 4, further including a casing for containing the generator means, the induction means and the tuning means.

6. The apparatus according to claim 1, wherein said induction means comprise:

means for generating in the atmosphere a gas jet, the latter having a momentum flux; and modulation means, connected to the generator means and responsive to said voltage pulses, for pulsing the momentum flux with a frequency less than 15 Hz;

whereby subaudio acoustic pulses are induced in the atmosphere.

7. Apparatus for manipulating the nervous system of a subject, the subject having an ear, comprising:

generator means for generating voltage pulses;

a source of gas at a pressure different from the ambient atmospheric pressure;

a conduit having an orifice open to the atmosphere for passing a gaseous flux;

valve means, connected to the source of gas and the conduit to control the gaseous flux;

means, connected to the generator means and responsive to said voltage pulses, for operating the valve means to provide an oscillation of the gaseous flux with a frequency less than 15 Hz.

8. The apparatus according to claim 7, further comprising vessel means for smoothing fluctuations of the gaseous flux caused by fluctuations in the pressure of the source of gas.

9. A method for manipulating the nervous system of a subject, the subject having an ear, comprising the steps of:

generating voltage pulses; and inducing, in a manner responsive to the voltage pulses, at the ear subliminal atmospheric acoustic pulses with a pulse frequency less than 15 Hz.

10. The method according to claim 9, for exciting in the subject a sensory resonance that occurs at a resonance frequency less than 15 Hz, further comprising the step of tuning the pulse frequency to the resonance frequency.

11. The method according to claim 9, wherein said inducing comprises the steps of:
   generating in the atmosphere a gas jet, the latter having a momentum flux; and
   modulating the momentum flux in pulse-wise fashion in a manner responsive to the voltage pulses.

12. The method according to claim 11, further comprising the step of directing the gas jet at a material surface.

13. The method according to claim 9, wherein said inducing comprises the steps of:
   generating a gas flow through a conduit orifice that is open to the atmosphere; and
   modulating the gas flow to produce flow pulsations, in a manner responsive to the voltage pulses.

14. A method for remotely manipulating the nervous system of a subject in the course of law enforcement in a standoff situation, the subject having an ear, comprising the steps of:
   generating voltage pulses;
   generating, in a manner responsive to the voltage pulses, atmospheric acoustic signals at a plurality of locations remote from the subject for inducing at the ear subliminal atmospheric acoustic pulses with a pulse frequency less than 15 Hz, the signals having phase differences with respect to each other arranged to cause constructive acoustic wave interference at the subject.

15. A method for exciting in a subject a sensory resonance having a resonance frequency less than 15 Hz, the subject having an ear, comprising the steps of:
   generating voltage pulses;
   inducing, in a manner responsive to the voltage pulses, at the ear subliminal atmospheric acoustic pulses with a pulse frequency less than 15 Hz;
   tuning the pulse frequency to the resonance frequency; and also
   inducing audible audio-frequency atmospheric acoustic signals at the ear.

16. A method for controlling in a subject neurological disorders that involve pathological oscillatory activity of neural circuits, the subject having an ear, comprising the steps of:
   generating voltage pulses;
   inducing, in a manner responsive to the voltage pulses, at the ear subliminal atmospheric acoustic pulses with a pulse frequency less than 15 Hz; and
   arranging said pulse frequency to detune the pathological oscillatory activity.

17. A method for controlling in a subject epileptic seizures, the subject having an ear, comprising the steps of:
   generating voltage pulses;
   inducing in a manner responsive to the voltage pulses, at the ear subliminal atmospheric acoustic pulses with a pulse frequency less than 15 Hz; and
   initiating said inducing when a seizure precursor is felt by the subject.

* * * * *